(12) United States Patent
Cho et al.

(10) Patent No.: US 10,792,309 B2
(45) Date of Patent: Oct. 6, 2020

(54) CELL THERAPY COMPOSITION FOR PREVENTING OR TREATING IMMUNE DISEASE COMPRISING MESENCHYMAL STEM CELLS AND IMMUNOREGULATORY T-CELLS AS ACTIVE INGREDIENT

(71) Applicant: CATHOLIC UNIVERSITY INDUSTRY ACADEMIC COOPERATION FOUNDATION, Seoul (KR)

(72) Inventors: Mi La Cho, Seoul (KR); Seok-Goo Cho, Seoul (KR); Jung-Yeon Lim, Seoul (KR); Hyun-Sil Park, Seoul (KR); Min-Jung Park, Incheon (KR)

(73) Assignee: CATHOLIC UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 1054 days.

(21) Appl. No.: 13/966,153

(22) Filed: Aug. 13, 2013

(65) Prior Publication Data
US 2017/0239295 A1    Aug. 24, 2017

Related U.S. Application Data

(63) Continuation-in-part of application No. PCT/KR2012/001194, filed on Feb. 17, 2012.

(30) Foreign Application Priority Data

Feb. 18, 2011  (KR) ...................... 10-2011-0014398

(51) Int. Cl.
| | | |
|---|---|---|
| *C07K 14/715* | (2006.01) | |
| *A61K 35/28* | (2015.01) | |
| *C12N 5/0783* | (2010.01) | |
| *C12N 5/0775* | (2010.01) | |
| *A61K 31/21* | (2006.01) | |
| *A61K 39/00* | (2006.01) | |
| *A61K 35/17* | (2015.01) | |

(52) U.S. Cl.
CPC .............. *A61K 35/28* (2013.01); *A61K 31/21* (2013.01); *A61K 35/17* (2013.01); *A61K 39/001* (2013.01); *C12N 5/0637* (2013.01); *C12N 5/0667* (2013.01); *A61K 2039/5158* (2013.01); *C12N 2501/15* (2013.01); *C12N 2501/51* (2013.01); *C12N 2501/515* (2013.01)

(58) Field of Classification Search
None
See application file for complete search history.

(56) References Cited

U.S. PATENT DOCUMENTS

| | | | | |
|---|---|---|---|---|
| 2006/0115899 A1* | 6/2006 | Buckner | ............ | A61K 39/0008 435/372 |
| 2010/0172885 A1* | 7/2010 | Pittenger | ................. | A61P 35/00 424/93.7 |

FOREIGN PATENT DOCUMENTS

WO    WO 2012/111997 A2 *  8/2012

OTHER PUBLICATIONS

Itoh, M. et al, "Thymus and Autoimmunity: Production of CD25+ CD4+ Naturally Anergic and Suppressive T Cells as a Key Function of the Thymus in Maintaining Immunologic Self-Tolerance," J Immunol, 1999, vol. 162, pp. 5317-5326.*
Sakaguchi, S. et al, "Regulatory T Cells and Immune Tolerance," Cell, May 30, 2008, vol. 133, pp. 775-787.*
Hippen et al,, "Clinical Perspectives for Regulatory T Cells in Transplantation Tolerance," Seminars in Immunology, vol. 23, No. 6, 2011, pp. 462-468.*
Morris et al., "Naturally-existing CD4+CD25+Foxp3+ regulatory T cells are required for tolerance to experimental autoimmune thyroiditis induced by either exogenous or endogenous autoantigen," Journal of Autoimmunity, vol. 33, No. 1, Aug. 2009, pp. 68-76.*
McMurray et al., 1997; Semin Arthritis Rheum 26:689-701 Hepatitis C Virus Infection and Autoimmunity.*

* cited by examiner

*Primary Examiner* — Maria G Leavitt
(74) *Attorney, Agent, or Firm* — Sughrue Mion, PLLC

(57) ABSTRACT

The present invention relates to a cell therapy composition for preventing or treating immune disease comprising mesenchymal stem cells and immunoregulatory T-cells as an active ingredient. By infusing mesenchymal stem cells and immunoregulatory T-cells, which are the cellular therapeutic agent of the present invention, into bone marrow transplant animals, rejection to the host is suppressed after the engraftment of the transplanted bone-marrow to thus obtain the effect of reducing graft-versus-host disease and immune disease. Moreover, the effect of such GVHD reduction is much greater than the one obtained when only mesenchymal stem cells are infused. Accordingly, the cell therapy composition of the present invention having the above-mentioned effects can be useful in the prevention or treatment of immune disease.

4 Claims, 7 Drawing Sheets

CELL THERAPY COMPOSITION FOR PREVENTING OR TREATING IMMUNE DISEASE COMPRISING MESENCHYMAL STEM CELLS AND IMMUNOREGULATORY T-CELLS AS ACTIVE INGREDIENT

TECHNICAL FIELD

The present invention relates to a cellular therapeutic agent for preventing for treating immune disease, and more particularly, to a cell therapy composition far preventing or treating immune disease comprising mesenchymal stem cells and immunoregulatory T-cells as an active ingredient.

BACKGROUND ART

Graft-versus-host disease (GVHD) refers to a disease wherein the body of the patient has an immune reaction to the donor's peripheral blood or the T lymphocytes in the bone marrow that are injected during homogeneous transplantation. Namely, it is a disease that is induced by living lymphocytes which were transfused causing an immune reaction that leads to problems in liver function, skin lesions, jaundice, diarrhea, fever, pancytopenia, and so on, and in severe cases patient death.

Graft-versus-host disease can be classified largely into acute graft-versus-host disease (aGVHD) and chronic graft-versus-host disease (cGVHD).

cGVHD in the case of homogenous transplantations, occurs usually 4-6 months following transplantation and its occurrence within 80 days or after 1 year is uncommon. Accordingly, it can be seen that a homogeneous reaction is a major pre-requisite for causing cGVHD and the pathogenesis of cGVHD goes through a long incubation period or the effect on the target organ shows up slowly.

aGVHD is an important complication of allogencic hematopoietic cell transplantation, which occurs mostly within 30 to 40 days after allogeneic hematopoietic stem cell transplantation, and involves the infiltration of inflammatory cells into the skin, liver, and gastrointestinal tract. The disease emerges in three phases. The first phase emerges prior to the bone marrow transplant: the patient's tissues are harmed, and in some cases, antigen-presenting cells are activated due to bacterial infection. In the second phase, the T-cells among the transplanted bone marrow cells are activated. The patient's antigen-presenting cells, which have already been activated, differentiate the T-cells into Th1 cells, and ultimately produce cytokines such as IL-2 and IFN-gamma. In the third phase, the patient's organ is disrupted. When the cytotoxic T-cells and natural killer cells are activated by the cytokine that is secreted from the activated Th1 cells, they attack the organ of the patient and generate acute graft-versus-host disease.

Several method have been suggested to treat acute graft-versus-host disease. Some of the suggested methods are as follows: removing T-cells from the bone marrow cells that are being transplanted, administering antibodies to CD80 and CD86 in order to control the responses of the T-cells and antigen-presenting cells, administering antibodies against cytokines such as IL-2 and IFN-gamma, or administering compound immunosuppressive such as cyclosporin A, rapamycin and FK-506 steroid medicine. Among these methods, administering compound immunosuppressive to restrain the activation of T-cells has been the most widely adopted.

A wide range of compound immunosuppressive has been developed at present. Among these, cyclosporin A has shown the most excellent clinical effects, and has been widely used to treat acute graft-versus-host disease, autoimmune diseases, organ transplant rejection and various inflammatory diseases. When a large volume of cyclosporin A is used, it can perfectly suppress the activation of T-cells and treat the disease. However, it will also cause serious side effects, including kidney toxicity. Thus, it is recommended that only a small amount of cyclosporin A be administered.

Mesenchymal stem cells (MSC) are stem cells residing throughout the body including bone marrow, which can differentiate into a variety of cell lineages such as fat cells, bone cells, and cartilage cells. MSCs are separated from many species including humans, mice, rats, dogs, goats, rabbits, and cats. It was recently reported that MSCs exhibit immunomodulating capacity by suppressing the activation of a variety of T-lymphocytes in vitro and in vivo; however, the mechanisms involved in the immunoregulatory activity MSCs on T lymphocytes are still partially obscure.

Moreover, no report has been found regarding the use of MSCs together with other cells shows a greater effect in treating GVHD, as compared to the use of only MSCs.

Thus, the inventors of this invention have completed this invention by confirming that, when mesenchymal stem cells and immunoregulatory T-cells are infused into bone marrow transplanted animals, rejection to the host is suppressed after the engraftment of transplanted bone-marrow to thus obtain a GVHD reducing effect, and this effect is much greater than the one obtained when only mesenchymal stem cells are infused.

DISCLOSURE OF INVENTION

Technical Problem

Accordingly, it is an object of the present invention to provide a cellular therapeutic agent for effectively preventing or treating graft-versus-host disease without the use of an immunosuppressive agent.

Solution to Problem

To accomplish the aforementioned object of the present invention, there is provided a cell therapy composition for preventing or treating immune disease comprising mesenchymal stem cells and immunoregulatory T-cells as an active ingredient.

In one, embodiment of the present invention, the mesenchymal stem cells may be human-derived mesenchymal stem cells.

In one embodiment the present invention, the regulatory T-cells may be immunoregulatory T-cells induced be retinal.

In one embodiment of the present invention, the immunoregulatory T-cells induced by retinal may be CD4+CD25+ immunoregulatory induced by treating CD4+ T-cells with anti-CD3, TGF-b, anti-CD28, and retinal.

In one embodiment of the present invention, the composition may include a cellular therapeutic agent of $1\times10^4$ cell/kg to $1\times10^8$ cell/kg.

In one embodiment of the present invention, the immune disease may be selected from the group consisting of graft versus host disease, autoimmune disease, rheumatoid arthritis, lupus, Behcet's disease, and Sjogren syndrome.

Furthermore, the present invention provides a method for preventing or treating immune disease, the method including the step of administering a composition comprising mesenchymal stem cells and immunoregulatory T-cells in an individual requiring the composition.

In one embodiment of the present invention, the regulatory T-cells may be immunoregulatory T-cells induced by retinal, and the immunoregulatory T-cells induced by retinal may be CD4+CD25+ immunoregulatory T-cells induced by treating CD4+ T-cells with anti-CD3, TGF-b, anti-CD28, and retinal.

In one embodiment of the present invention, the immune disease may be selected from the group consisting of graft versus host disease, autoimmune disease, rheumatoid arthritis, lupus, Behcet's disease, and Sjogren syndrome.

Furthermore, the present invention provides a customized kit for preventing or treating immune disease, the kit including a composition comprising mesenchymal stem cells and immunoregulatory T-cells as an effective ingredient.

In one embodiment of the present invention, the regulatory T-cells may be immunoregulatory T-cells induced by retinal, and the immunoregulatory T-cells induced by retinal may be CD4+CD25+ immunoregulatory T-cells induced by treating CD4+ T-cells with anti-CD3, TGF-b, anti-CD28, and retinal.

In one embodiment of the present invention, the immune disease may be selected from the group consisting of graft versus host disease, autoimmune disease, rheumatoid arthritis, lupus, Behcet's disease, and Sjogren syndrome.

Advantageous Effects of Invention

By infusing mesenchymal stem cells and immunoregulatory T-cells, which are the cellular therapeutic agent of the present invention, into bone marrow transplant animals, rejection to the host is suppressed after the engraftment of transplanted bone-marrow to thus obtain the effect of reducing graft-versus-host disease and immune disease.

Moreover, the effect of such GVHD reduction is much greater than the one obtained when only mesenchymal stem cells are infused.

Accordingly, the therapy composition of the present invention having the above-mentioned effects can be useful in the prevention or treatment of immune disease.

BRIEF DESCRIPTION OF DRAWINGS

The above and other objects and features of the present invention will become apparent from the following description of the preferred embodiments given in conjunction with the accompanying drawings, in which.

BEST MODE FOR CARRYING OUT THE INVENTION

Figure 1:
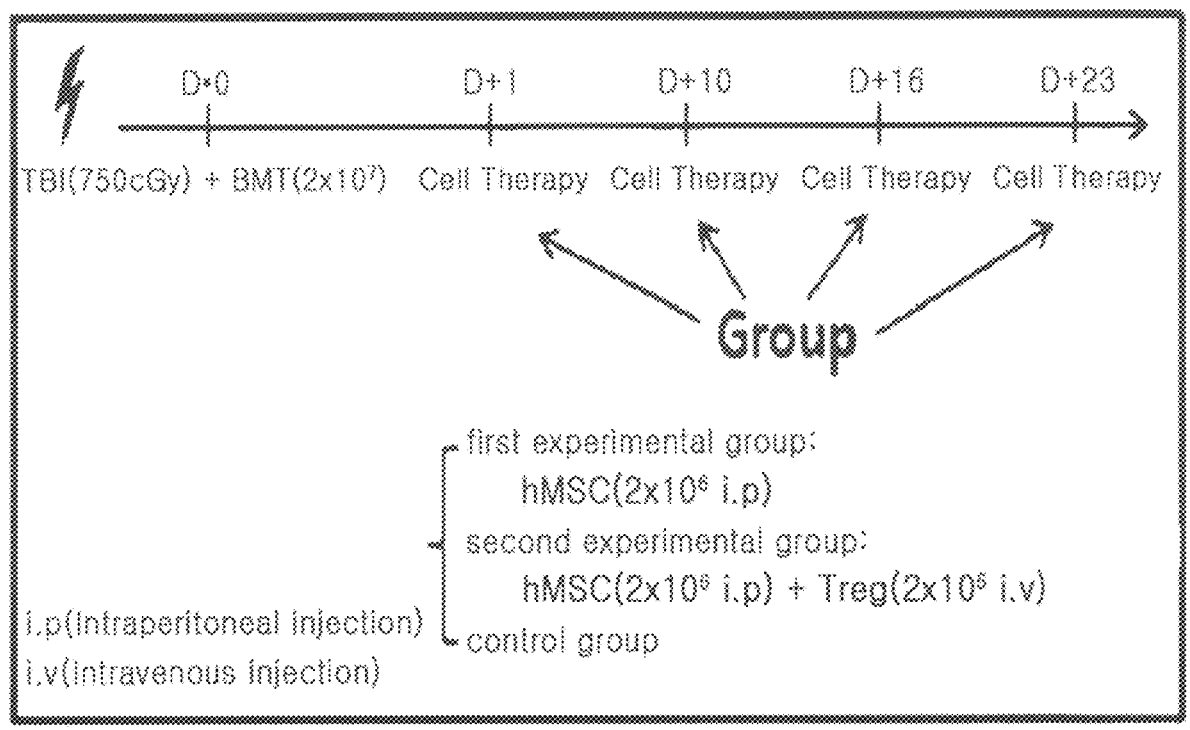
FIG. 1 shows a brief schematic view of the cell therapy schedule of an acute graft-versus-host disease animal model (hMSC: human-derived mesenchymal stem cells, Treg: immunoregulatory T-cells)

The present invention provides a cell therapy composition for preventing or treating graft-versus-host disease comprising mesenchymal stem cells and immunoregulatory T-cells as an active ingredient.

As used herein, the term "mesenchymal stem cells (MSC)" refer to stem cells derived from bone marrow, blood, dermis, and periosteum, refer to pluripotent multipotent cells which have the ability to differentiate into various cells, including fat cells, cartilage cells, and bone cells.

As used herein, the term "immunoregulatory T-cells" refers to a kind of T-cells which have the characteristics that inhibit the function of abnormally activated immune cells and control inflammatory responses, and are referred to as regulatory T-cells (Treg). The immunoregulatory T-cells may be classified into natural Treg and adaptive Treg, CD+CD25+ T-cells, which are natural Treg, are endowed with immunosuppressive function since when these cells are produced from the thymus gland, and constitute 5 to 10% of peripheral CD4+ lymphocyte in a normal individual. Although the immunosuppressive mechanism of the CD+CD25+ T-cells have not been clarified so far, an expression control element of a gone called Foxp3 have been recently found to play an important role in the differentiation and activation of these cells. Moreover, peripheral natural T-cells can be differentiated into cells which exert an immunosuppressive effect when stimulated by autoantigen or external antigen under a specific environment. These cells are called adaptive Treg or inducible treg, and include Th3, CD8 Ts, etc which secretes IL-1secreting Tr1 and TGF-β.

As used herein, the term "retinal" refers to a reduced form of retinol or vitamin A, which is an essential nutrient which exerts various biological functions. The chemical name is 3,7-dimethyl-9-(2,6,6-trimethyl-1-cyclohexenyl-1-yl)-2,4,2,6,8-nonatetraenal.

As used herein, the term "cellular therapeutic agent" refers to a drug used for the purpose of treatment, diagnosis and prevention through a series of behaviors of in vitro multiplying and sorting living autologous, allogenic and xenogenic cells or changing the biological characteristics of cells by other means for the purpose of recovering the functions of cells and tissues. Cellular therapeutic agents have been considered drugs since 1993 in the U.S. and since 2002 in South Korea. Such cellular therapeutic agents may be roughly classified into two categories: "stem cell therapeutic agents" for tissue regeneration or organ function recovery and "immune cell therapeutic agents" for the suppression of in vivo immune response or the regulation of immune response such as hyper immune response.

Mesenchymal cells used in the present invention may be derived from animal, preferably from mammalian, more preferably from human. The mesenchymal stem cells of the present invention can be isolated from bone marrow, adipose tissue, peripheral blood, liver, lung, amniotic fluid, chorionic villi of the placenta and umbilical cord blood, particularly preferably, human adipose tissue.

Although The mesenchymal stem cells are present in bone marrow in very minute amounts and the general procedures for isolating and culturing mesenchymal stem cells are well-known in the art (which is disclosed, for example, its the U.S. Pat. No. 5,486,359), and the mesenchymal stem ells can be obtained by a known method by being isolated from stem cells in bone marrow using their attachment characteristic and cultured while their ability to differentiate is not lost.

The procedures for obtaining mesenchymal stem cells will be described as follows. Mesenchymal stem cells can be obtained through the steps of (1) isolating mesenchymal stem cells from mammalian including human and mouse, preferably from a human source such as blood or bone marrow, (the bone marrow can be derived from tibiae, femurs, spinal cord, or ilium); (2) culturing the isolated cells in a suitable medium; and (3) removing floating cells in the culturing process and sub-culturing the cells attached to a culture plate, thus resulting in established mesenchymal stem cells.

A medium useful in the above procedure includes any conventional medium for culturing stem cells, preferably, a medium containing serum (e.g., fetal bovine serum, horse serum and human serum). The medium used in this invention includes, for example, RPMI series (e.g., RPMI 1640), Eagles's MEM (Eagle's minimum essential medium, Eagle, H. Science 130:432(1959)), α-MEM (Stanner, C P. et al., Nat. New Biol. 230:52(1971)), Iscove's MEM (Iscove, N. et al., J. Exp. Med. 147:923(1978)), 199 medium (Morgan et al., Proc. Soc. Exp. Bio. Med. 73:1(1950)), CMRL 1066, RPMI 1640 (Moore et al., J. Amer. Med. Assoc. 199:519 (1967)), F12 (Ham, Proc. Natl. Acad. Sci. USA 53:288 (1965)), FIO (Ham, R. G. Exp. Cell Res. 29:515(1963)), DMEM (Dulbecco's modification of Eagle's medium Dulbecco, R. et al., Virology 8:396(1959)), Mixture of DMEM and F12 (Barnes, D. et al., Anal. Biochem. 102:255(1980)), Way-month's MB752/1 (Waymouth, C. J. Natl. Cancer Inst. 22:1003(1959)); McCoy's 5A (McCoy, T. A., et al., Proc. Soc. Exp. Biol. Med. 100:115(1959) and MCDB series (Ham, R. G. et al., In Vitro 14:11(1978)) but not limited thereto. The medium may contain other components, for example, antibiotics antifungal agent (e.g., penicillin, streptomycin), glutamine, and so on.

The mesenchymal stem cells can be identified by using flow cytometry which may be carried out with specific surface markers of MSCs. For example, mesenchymal stem cells are positive for CD44, CD29 and MHC class I, the MSCs can be identified through these surface markers.

The immunoregulatory T-cells used in the present invention may be preferably, though not limited to, immunoregulatory T-cells induced by retinal.

The process of obtaining immunoregulatory T-cells induced by retinal will be described in detail by the following steps: (1) preparing CD4+ T-cells; (2) plating the CD4+ T-cells prepared in the step (1) and irradiated antigen presenting cells (APC) on a well plate coated with anti-CD3, and then treating them with anti-CD28 antibody and TFGβ to establish a differentiation environment; and (3) obtaining CD4+CD25+ immunoregulatory T-cells by treating the cells having undergone the step (2) with a retinal compound.

In the step (1), the CD4+ T-cells may be CD4+ T-cells isolated from spleen cells.

In the step (2), the plated CD4+ T-cells and the irradiated antigen presenting cells may be $5 \times 10^5$ cells, respectively.

In the step (2), the intensity of radiation on the antigen presenting cells may be 5,000 rad.

In the step (2), the concentration of the coated anti-CD3 may be 1 μg/mL.

In the step (2), the concentration of the treated anti-CD28 antibody may be 1 μg/mL, and the concentration of the treated TGFβ may be 5 ng/mL.

In the step (3), the concentration of the treated retinal may be from 0.1 λM to 1 μM.

In the step (3), the retinal compound may be used in the form of salt, preferably, a pharmaceutically acceptable salt.

Preferably, the salt includes an acid addition salt formed with a pharmaceutically acceptable free acid. Such free acids include organic acids and inorganic acids. Particular examples of the organic acids include, but are not limited to: citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluene sulfonic acid, glutainic acid and aspartic acid. Additionally, particular examples of the inorganic acids include, but are not limited to: hydrochloric acid, hydrobromic acid, sulfuric acid and phosphoric acid. Such a retinal compound may be isolated from a natural source. Otherwise, the retinal compound may be prepared by a chemical synthetic process known to those skilled in the art.

The cellular therapeutic composition of the present invention is in the form of a mixture of mesenchymal stem cells and immunoregulatory T-cells. That is, the mesenchymal stem cells and the immunoregulatory T-cells may be used in combination, rather than being used each alone.

In the present invention, it was confirmed by experiment that, when the mesenchymal stem cells and the immunoregulatory T-cells are used in combination, symptoms of immune disease can be reduced more effectively than the use of the mesencymal stem cells alone.

More specifically, in the following embodiment of the present invention, an acute graft-versus-host disease animal model was established by isolating stem cells from the femurs and tibiae of donor mice and transplanting them into recipient mice preconditioned with total-body irradiation (TBI). In the thus-established animal model, human mesenchymal stem cells ($2 \times 10^6$) were injected into the abdominal cavities of the mice, and at the same time, immunoregulatory T-cells ($2 \times 10^6$) induced by retinal were injected into the veins of the mice. The result shows that clinical graft-versus-host disease score was significantly lowered in the acute GVHD animal model.

Accordingly, when the cellular therapeutic agent (mesenchymal stem cells and immunoregulatory T-cells) of the present invention is infused into bone marrow transplanted animals, rejection to the host is suppressed after the engraftment of transplanted bone-marrow to thus inhibit the symptoms of immune disease such as graft-versus-host disease, and the cell therapy composition of the present invention having the above-mentioned effect is useful in the prevention or treatment of immune disease.

For reference, the term "engraftment" refers to the survival or proliferation of cells for treatment as implanted or transplanted cells for treatment (cell therapeutic agent) remain in a target organ (bone marrow, damaged organs, peripheral lymph nodes, tumor tissues, etc.) even after the lapse of a certain amount of time.

The cell therapy composition of the present invention having the above-mentioned effect is effective in preventing or treating immune disease, and the immune disease may be selected from, but not limited to, the group consisting of graft versus host disease, autoimmune disease, rheumatoid arthritis, lupus, Behcet's disease, and Sjogren syndrome.

The cell the agent of the present invention may be administered by any conventional routes that can reach a target tissue. Methods of administration include, without limitation, parenteral administration, for example, intraperitoneal administration, intravenous administration, intramuscular administration, subcutaneous administration, and intradermial administration.

The composition can be formulated in a suitable form together with a pharmaceutically acceptable carrier conventionally used for cell treatment. As used herein, the term "pharmaceutically acceptable" refers to a physiologically acceptable composition which, when administered to human beings, will generally not cause allergic reactions, such as gastrointestinal disturbance, dizziness, and similar reactions. Examples of the pharmaceutically acceptable carrier include carriers for parenteral administration, such as water, appropriate oil, saline solution, aqueous glucose, and gycol. Additionally, the parenteral administration carrier includes a stabilizer and a preserver. The stabilizer preferably includes antioxidant, such as sodium bisulfate, sodium sulfite and ascorbic acid. The preserver preferably includes benzalkonium chloride, methyl- or propyl-paraben and chloro butanol. Other pharmaceutically acceptable carriers are disclosed in the following reference (Remington's Pharmaceutical Science, 19th Edition, Mack Publishing Company, Easton, Pa., 1995).

Moreover, the composition may be administered by an arbitrary device capable of moving the cell therapeutic agent to target cells.

The cell therapy composition of the present may include a therapeutically effect amount of cell therapeutic agent for the treatment of disease. As used herein, the term "therapeutically effective amount" refers to an amount of an active ingredient or pharmaceutical composition that will elicit the biological or medical response of a tissue system, animal or human that is being sought by a researcher, veterinarian, medical doctor or clinician, and encompasses an amount of the active ingredient or pharmaceutical composition which will relieve the symptoms of the disease or disorder being treated. As will be apparent to those skilled in the art, the therapeutically effective amount of the cell therapeutic agent included in the composition of the present invention may vary depending upon desired therapeutic effects. Therefore, an optimal dose of the cell therapeutic agent to be administered can be easily determined by those skilled in the art. For example, an effective amount of the cell therapeutic agent is determined taking into consideration various factors such as kinds of disease, severity of disease, contents of active ingredients and other components contained in the composition, kinds of formulations, age, weight, health status, sex and dietary habits of patients, administration times and routes, release rates of the composition, treatment duration, and co-administered drugs.

For example, an effective amount of the composition of the present invention may be in a range of $1 \times 10^4$ cell/kg to $1 \times 10^8$ cell/kg.

Furthermore, the present invention provides a composition comprising, as an active ingredient, a cell therapeutic agent (mesenchymal stem cells and immunoregulatory T-cells) to prepare a drug for preventing or treating immune disease. The composition of the present invention comprising the cell therapeutic agent (mesenchymal stem cells and immunoregulatory T-cells) as an active ingredient may be used for the purpose of preparing a drug for preventing or treating immune disease.

Furthermore, the present invention provides a customized kit for preventing or treating immune disease, the kit including a composition comprising mesenchymal stem cells and immunoregulatory T-cells as an effective ingredient. The kit may be prepared by a kit preparation method used in the art, except that the kit may include mesenchymal stem cells and immunoregulatory T-cells as an active ingredient for inducing therapeutic effects.

Furthermore, the present invention provides a method for preventing or treating immune disease, the method including administering a therapeutically effective amount of cell therapeutic agent (mesenchymal stem cells and immunoregulatory T-cells) to a mammal.

As used herein, the term, "mammal" refers to any mammalian species that is in need of treatment, examination or experiment, preferably human.

In the treating method of the present invention, when the cell therapy composition of the present invention is administered once to several times a day, for example, to an adult, an effective amount of cell therapeutic agent (mesenchymal stem cells and immunoregulatory T-cells) included in the composition may be preferably in a range of $1 \times 10^4$ cell/kg to $1 \times 10^8$ cell/kg.

In the treating method of the present invention, the composition comprising the cell therapeutic agent (mesenchymal stem cells and immunoregulatory T-cells) of the present invention as an active ingredient may be administered in a conventional manner via a rectal, intravenous, intraarterial, intraperitoneal, intramuscular, intrasternal, percutaneous, local, intraocular, or intradermal route.

Advantages and features of the present invention, and implementation methods thereof will be clarified through following examples described with reference to the accompanying drawings. Hereinafter, the present invention will be described in detail by examples. It is to be understood, however, that these examples are for illustrative purpose only, and are not construed to limit the scope of the present invention.

Example 1

Establishment of Acute Graft Versus Host Disease (aGVHD) Animal Model

To establish an Acute Graft versus host disease (aGVHD) model, recipient mice Balb/c (H-2k/d) were conditioned with 750 cGy total body irradiation (TBI), and stem cells were isolated from the femurs and tibias of donor mice C57BL/6 (H-2k/b) and $2 \times 10^7$ of stem cells, were transplanted into the recipient mice Balb/c (H-2k/d), thereby establishing an aGVHD model.

Example 2

Preparation of Mesenchymal Stem Cells and Immunoregulatory T-cells as Cellular Therapeutic Agent of the Invention <2-1> Isolation and Culture of Mesenchymal Stem Cells from Adipose Tissues Adipose tissues obtained by liposuction or surgical operation were washed ten times using PBS containing 10% penicillin-streptomycin to remove blood and other contaminants and dissected into 0.2-0.3 g sections. The adipose tissue sections were incubated in 37° C.-water bath (100 rpm) for 1 hr. A 100 μm mesh was used to separate a solution layer decomposed with collagenase from undecomposed pieces, followed by adding the same volume of FBS to the separated collagenase solution. The solution was centrifuged for 5 minutes at 4° C. and at 1200 rpm and the supernatant containing lipids and fat layer and the collagenase supernatant were removed. For removing residual collagenase-treated solution from precipitated MSC, MSCGM [mesenchymal stem cell growth media: MSC minimal medium (Cambrex, Walkersville, Md., USA), mesenchymal cell growth supplements (Cambrex, Walkersville, Md., USA), 4 mM L-glutamine and penicillin (0.025 unit/500 ml)/streptomycin (0.025 mg/500 ml)] was added to precipitated MSC and centrifuged at 4° C. and at 1200 rpm for 5 min. MSCGM is a DMEM (Dulbecco's modified Eagle's medium)-based medium containing bovine fetal bovine serum. Then, the supernatant was discarded and MSC prepared thus was inoculated into culture dishes, followed by culturing in 5% $CO_2$ incubator at 37° C. The medium was changed every second day.

<2-2> Preparation of Immunoregulatory T-Cells $5 \times 10^5$ CD4+ T-cells isolated from spleen cells of C57BL/6 and $5 \times 10^5$ antigen presenting cells (APC) irradiated at 5000 rad were plated in a 24-well plate coated with 1 μg/mL of anti-CD3, and treated with anti-CD28 antibody with a concentration of 1 1 μmg/mL of and TGfβ with a concentration of 5 ng/mL to induce regulatory differentiation for days. The cells were treated with retinal at concentrations of 0.1 uM and 1 uM before regulatory T-cell differentiation. For flow cytometry, anti-mouse CD4 PerCP, CD25 APC, and FoxP3 PE-labeled Abs were incubated at 4° C. for 30 minutes. The cells were washed with PBS and measured by a FACS caliber.

Example 3

Effects of Cellular Therapeutic Agent of the Invention on Acute Graft-Versus-Host Disease Animal Model <3-1> Clinical GVHD Scoring To examine the effects of the cellular therapeutic agent of the invention on acute graft-versus-host disease, clinical GVHD scores were measured for: a first experimental group in which mesenchymal stem cells ($2 \times 10^6$ intraperitoneal injection) alone derived from human fat prepared in Example <2-1> were infused; and a second experimental group in which mesenchymal stem cells ($2 \times 10^6$ intraperitoneal injection) derived from human fat prepared in Example <2-1> and immunoregulatory T-cells ($2 \times 10^6$ intravenous injection) prepared in Example <2-2>. Cell infusion was conducted 4 times and once a week (see FIG. 1). Additionally, a control group was used in which no treatment was done on the acute graft-versus-host disease animal model established in Example 1 at all.

The clinical GVHD scores were evaluated using a clinical scoring system in which the degree of progression of GVHD in mice is observed everyday by giving scores for weight reduction, fur condition, posture, intensity of activity, and changes in the skin of the feet or tail.

Figure 2:
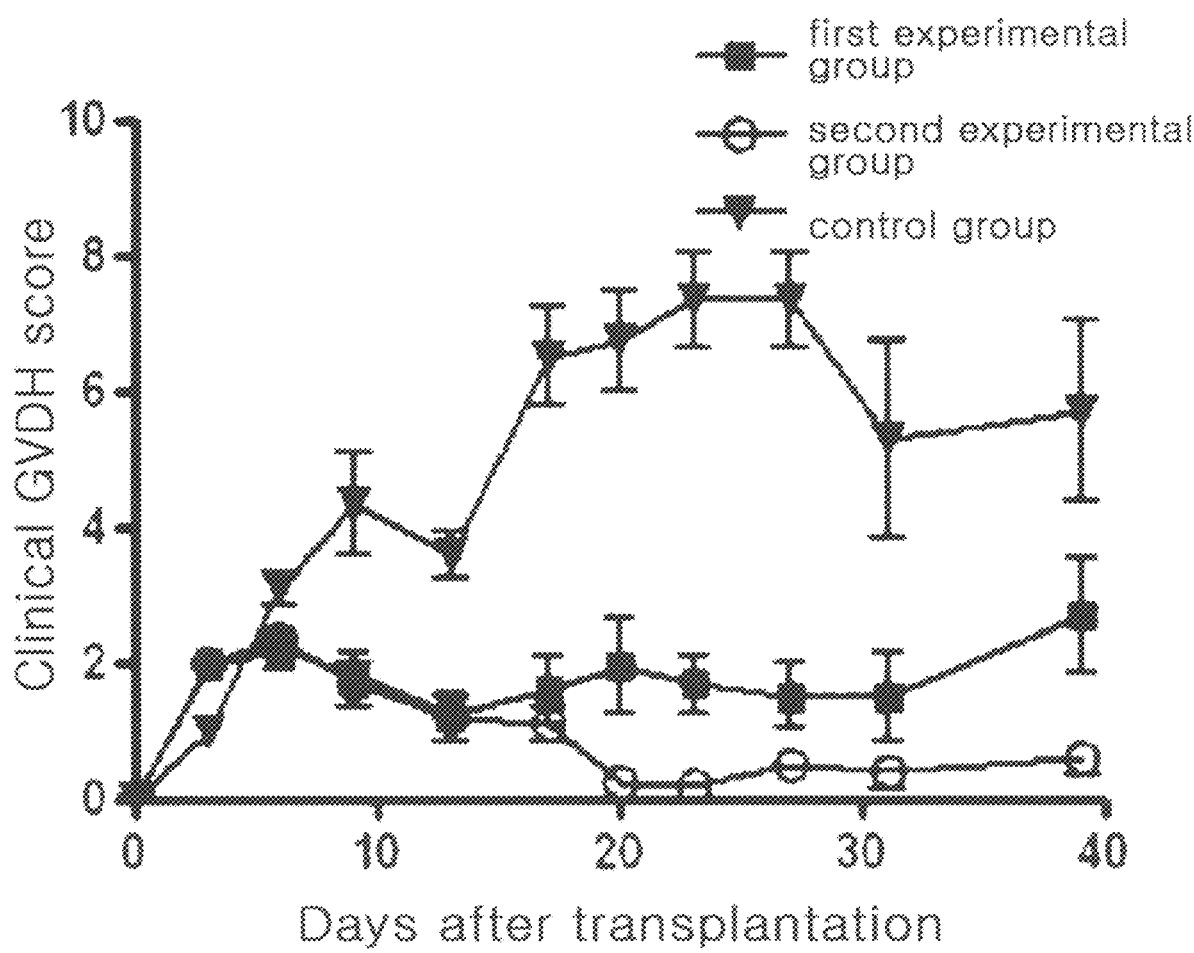
FIG. 2 is a graph showing the clinical GVHD scores of a group (first experimental group) treated with mesenchymal stem cells alone and a group (second experimental group) infused with both mesenchymal stem cells and immunoregulatory T-cells in the acute graft-versus-host disease animal model.

As shown in FIG. 2, the result shows that, in the aGVHD model, the clinical GVHD score for the group (second experimental group) treated with mesenchymal stem cells and immunoregulatory T-cells was significantly lower than that for the group (first experimental group) treated with mesenchymal stem cells alone. From this result, it was proved that GVHD rarely occurs in the second experimental group. The control group scored highest in the clinical scoring system and was proved to be suitable for the aGVHD model.

Figure 3:
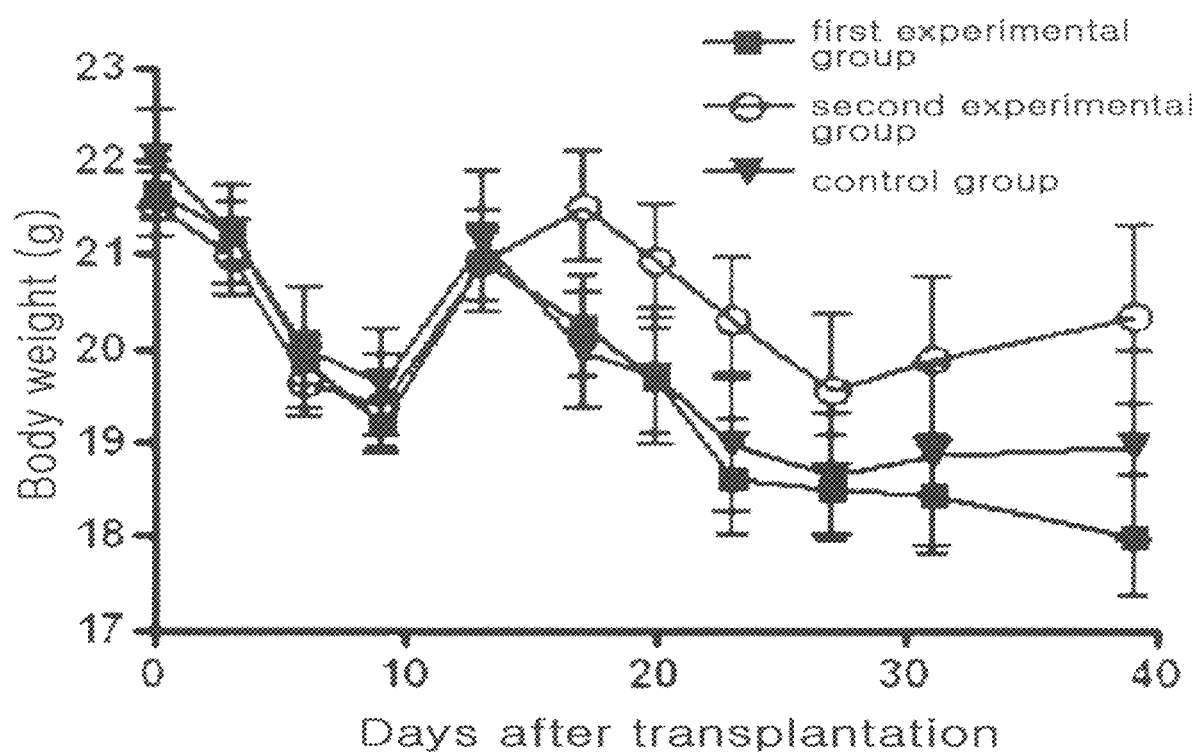
FIG. 3 is a graph showing the mice weight measurements of the group (first experimental group) treated with mesenchymal stem cells alone and the group (second experimental group) infused with both mesenchymal stem cells and immunoregulatory T-cells.

FIG. 3 shows the scores of the weight measurements of the mice. The second experimental group scored highest on weight. This can be regarded as an example of one aspect of overcoming GVHD.

<3-2> Histopathological Analysis of Skin, Small Intestine, Large Intestine, and Liver To examine the effects of the cellular therapeutic agent of the invention acute graft-versus-host disease front a histopathological viewpoint, the skin tissue, small intestine tissue, large intestine tissue, and liver tissue of each of the first experimental group, second experimental group, and control group were sectioned into slices, and then stained with bematoxylin/eosin (the first experimental group, second experimental group, and control group were killed 50 days after stem cell transplantation).

Figure 4:
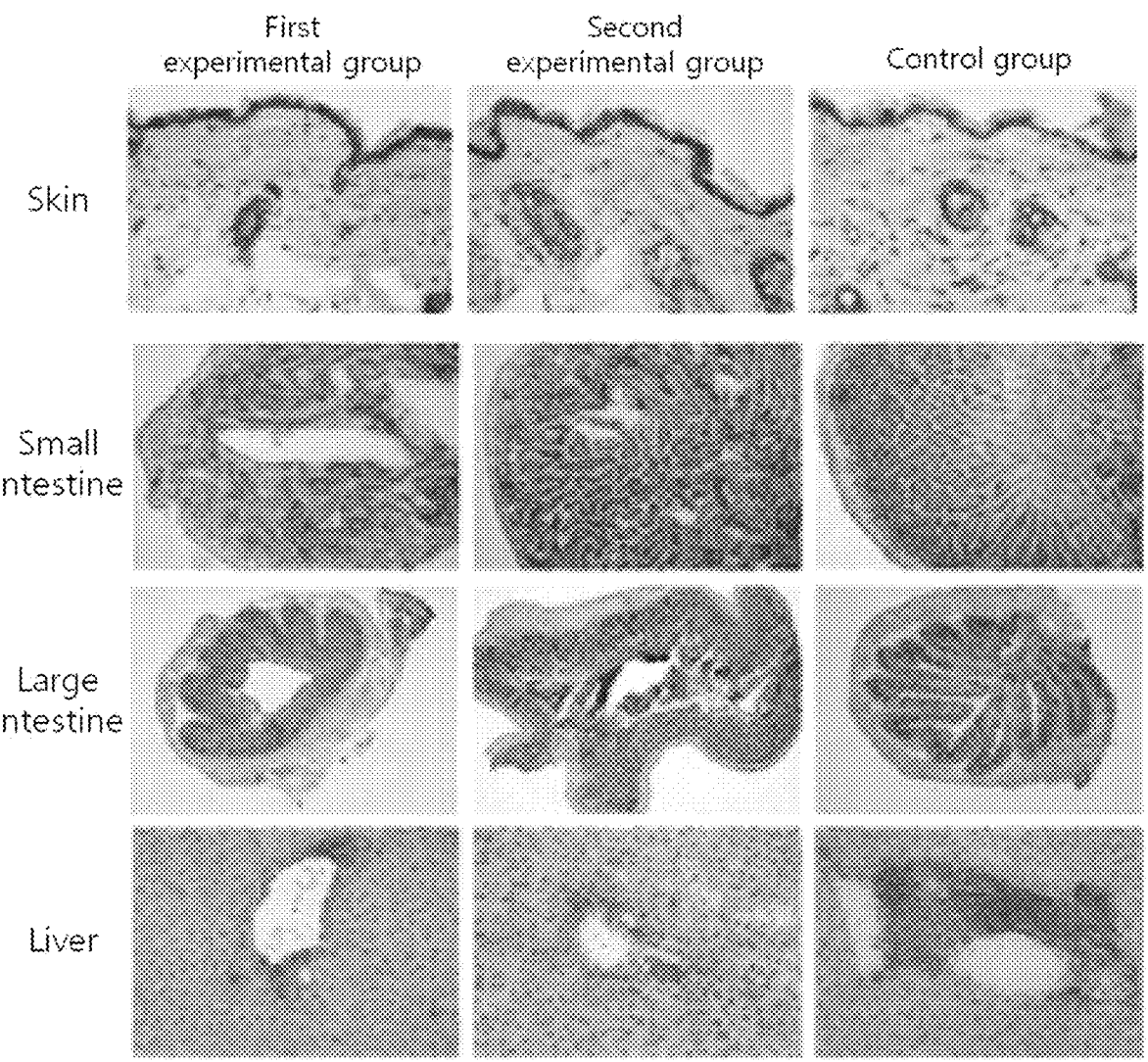
FIG. 4 is photographs of analysis of pathological tissue of the skin, small intestine, large intestine, and liver stained with hematoxylin/eosin in the group (first experimental group) treated with mesenchymal stem cells alone and the group (second experimental group) infused with both mesenchymal stem cells and immunoregulatory T-cells to the acute graft-versus-host disease animal model.

As a result, as shown in FIG. 4, it was observed that the control group was considered suitable for graft-versus-host disease because it showed lymphocytic infiltration into each organ and destruction of epithelium and mucous membrane, and that the lymphocytic infiltration into each organ and destruction of epithelium and mucous membrane in the second experimental group (group infused with mesenchymal stem cells and immunoregulatory T-cells) were significantly less compared to the first experimental group (group infused with mesenchymal stem cells). From this, it was proved that the cellular therapeutic agent mesenchymal stem cells and immunoregulatory T-cells) of the invention is a cell therapy capable of overcoming graft-versus-host disease.

Example 4

Establishment of Autoimmune Arthritis Animal Model

IL-1Ra knockout mice were prepared according to the method presented by Y. Iwakura team. In the IL-1Ra knockout mice, the iL-1 receptor antagonist (IL-1Ra) acts directly on the IL-1 receptor to prevent IL-1α and IL-1β from acting on the receptor, resulting in naturally causing autoimmune arthritis disease.

Example 5

Therapeutic Effects of Mesenchymal Stem Cell and Treg cell Treatment on Autoimmune Arthritis To examine whether the mesenchymal stem cell and immunoregulatory T-cell Treg treatment has therapeutic effects on autoimmune arthritis in the autoimmune arthritis animal model established in Example 4, firstly, normal Balb/c ($H-2k/^d$) were killed, single cells were isolated from the spleen, and then CD4T-cells where isolated using MACs Bead isolation. The CD4 T-cells were stimulated with 1 μg/ml of anti-CD3, 5 mg/ml of TGF-b, 1 uM of retinal, and 1 μg/ml of anti-CD28 and cultured for 3 days isolate Cd4+Cd25+ T (Treg) cells.

Afterwards, mesenchymal stem cells (Human MSCs $2 \times 10^6$ i.p) and the obtained Treg ($2 \times 10^6$ i.v) cells were infused a total of three times at weekly intervals into an IL-1RaKO mice model, which is the autoimmune arthritis model established in Example 4. A group infused with mesenchymal stem cells alone and a group treated with nothing were used as control groups. The severity of arthritis was scored and measured, and the degree of destruction of joints and cartilage each experimental mouse was observed in immunohistochemical staining. Further, the levels of production of Th2 type IgG1 and Th1 type IgG2a were measured.

Figure 5:
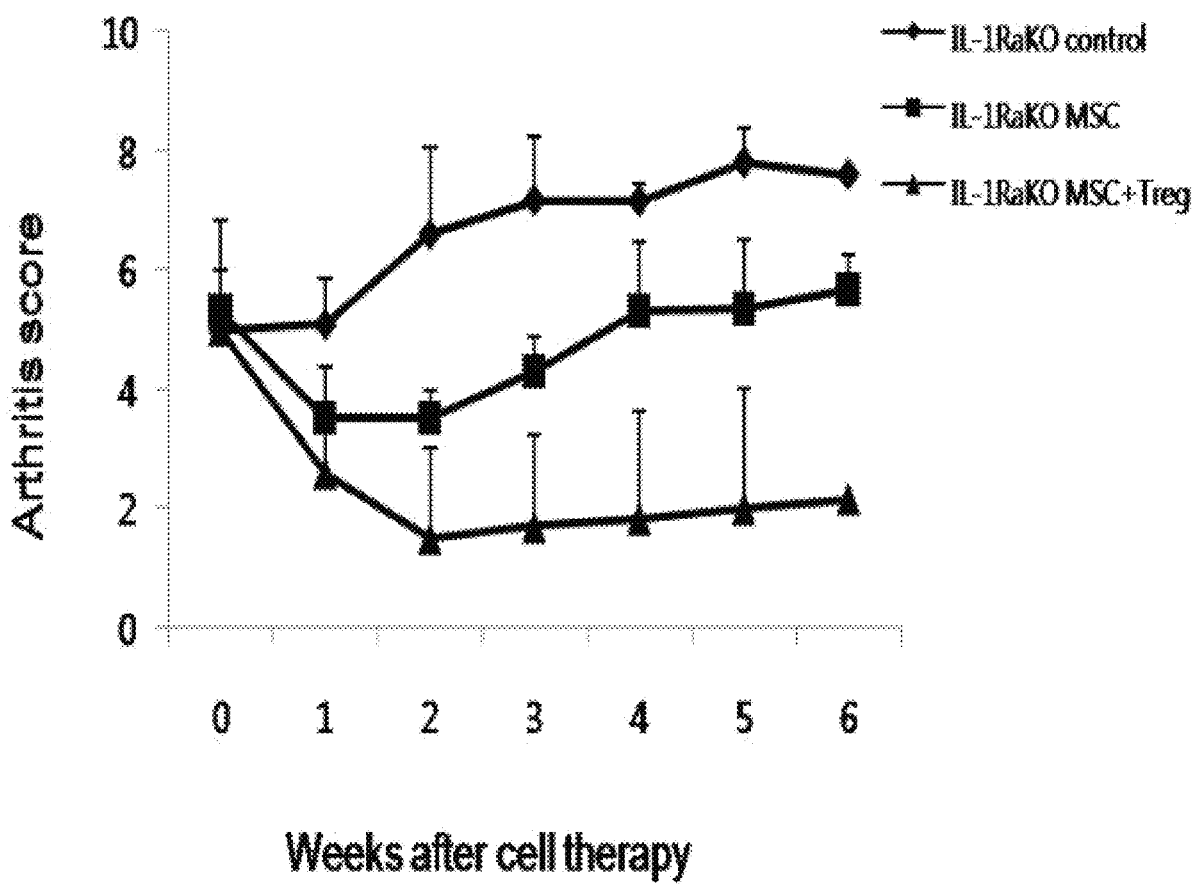
FIG. 5 shows the measurements of the severity of arthritis in the group treated with mesenchymal stem cells alone, the group treated with both mesenchymal stem cells and immunoregulatory T-cells, and a group treated with nothing in the acute graft-versus-host disease animal model.

As a result, as shown in FIG. 5, the severity of arthritis in mice with autoimmune arthritis treated with mesenchymal stem cells alone was lower than that in arthritis mice treated with nothing, and the severity of the disease in a group treated with both mesenchymal stem cells and treg cells was improved compared to the group treated with mesenchymal stem cells alone.

Figure 6:
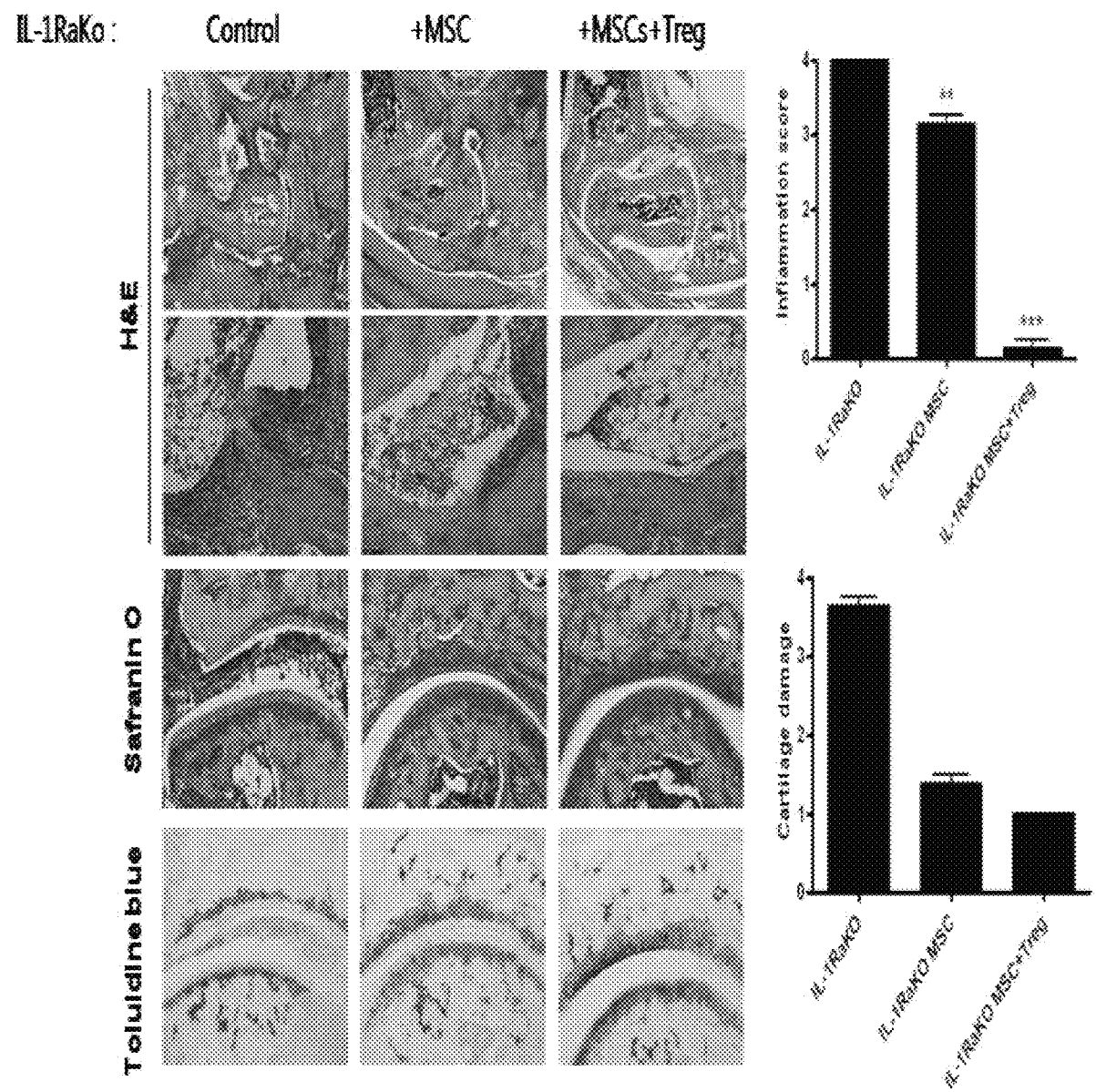
FIG. 6 shows the result of measuring the destruction of joints and cartilage and the level of infiltration of inflammatory cells by immunohistochemical staining in the group treated with mesenchymal stem cells alone, the group treated with both mesenchymal stem cells and immunoregulatory T-cells, and a group treated with nothing in the acute graft-versus-host disease animal model.
Figure 7:
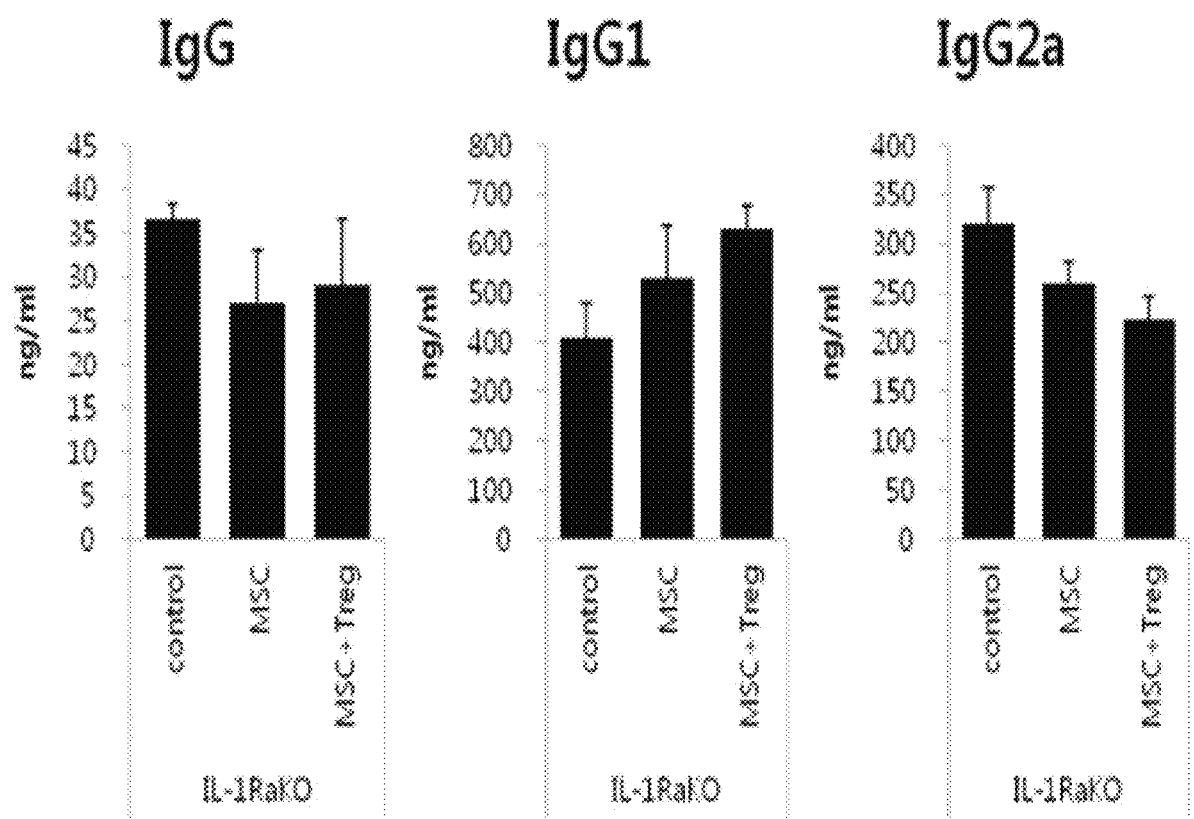
FIG. 7 is a graph showing the expression levels of IgG, IgG1, and IgG2a in the group treated with mesenchymal stem cells alone, the group treated with both mesenchymal stem cells and immunoregulatory T-cells, and a group treated with nothing in the acute graft-versus-host disease animal model.

The analysis result of immunohistochemical staining showed that the degree of destruction of joints and cartilage in the group treated with both mesenchymal stem cells and treg cells was significantly lower than the group treated with mesenchymal stem cells alone, and the infiltration of inflammatory cells was also reduced (see FIG. 6).

Further, the result of analysis of effects on Th1 and Th2 responses showed that the TH2 type IgG1 level of the group infused with both mesenchymal stem cells and immunoregulatory cells was increased but the Th1 type IgG2a level thereof was decreased. From these results, the present invention can conclude that treatment of both mesenchymal stem cells and immunoregulatory cells can greatly contribute to reduction in the inflammatory responses immune cells.

Although the invention has been described focusing on the preferred embodiments, those skilled in the art will appreciate that the invention may be carried out in modified forms without departing from the essential characteristics of the present invention. Therefore, the above embodiments should be construed in all aspects as illustrative and not restrictive. The scope of the invention should be determined by the appended claims and their legal equivalents, not by the above description, and all changes coming within the equivalency range of the appended claims should be construed as being embraced in the invention.

The invention claimed is:

1. A method for treating an immune condition where an enhancement of a Th2-mediated immune response and suppression of a Th1-mediated immune response are desired, said method comprising the step of administering to a subject in need thereof a therapeutically effective amount of a cellular therapeutic agent comprising mesenchymal stem cells and activated CD4+CD25+immunoregulatory T-cells, wherein the CD4+CD25+immunoregulatory T-cells are isolated CD4+ T-cells that have been activated through CD3/CD28 cell surface moieties, and contacted with Transforming growth factor beta (TGFβ) and 3,7-dimethyl-9-(2,6,6-trimethyl-1-cyclohexenyl-1-yl)-2,4,2,6,8-nonatetraenal, a pharmaceutically acceptable salt or isomer thereof.

2. The method of claim 1, wherein the mesenchymal stem cells are mesenchymal stem cells obtained from human.

3. The method of claim 1, wherein the cellular therapeutic agent comprises $1 \times 10^4$ cell/kg to $1 \times 10^8$ cell/kg.

4. The method of claim 1, wherein the immune condition is selected from the group consisting of graft versus host disease, autoimmune disease, rheumatoid arthritis, lupus, Behcet's disease, and Sjogren syndrome.

* * * * *